(12) United States Patent
Johnson et al.

(10) Patent No.: US 11,439,743 B2
(45) Date of Patent: Sep. 13, 2022

(54) INTRAVENOUS DEVICE ATTACHMENT MECHANISM FOR WAGONS

(71) Applicant: Radio Flyer Inc., Chicago, IL (US)

(72) Inventors: Mark Johnson, Chicago, IL (US);
Jason Fitzwater, Chicago, IL (US);
Jacob Swan, Chicago, IL (US)

(73) Assignee: Radio Flyer Inc., Chicago, IL (US)

( * ) Notice: Subject to any disclaimer, the term of this patent is extended or adjusted under 35 U.S.C. 154(b) by 37 days.

(21) Appl. No.: 16/951,113

(22) Filed: Nov. 18, 2020

(65) Prior Publication Data
US 2021/0146038 A1     May 20, 2021

Related U.S. Application Data

(60) Provisional application No. 62/936,926, filed on Nov. 18, 2019.

(51) Int. Cl.
*A61M 5/14*         (2006.01)
*B62B 5/00*         (2006.01)

(52) U.S. Cl.
CPC ............ *A61M 5/1415* (2013.01); *B62B 5/00* (2013.01); *A61M 2205/59* (2013.01); *A61M 2209/084* (2013.01)

(58) Field of Classification Search
CPC ............ A61M 5/1415; A61M 2205/59; A61M 2209/084; B62B 5/00; B62B 2203/44;
(Continued)

(56) References Cited

U.S. PATENT DOCUMENTS 2,696,963 A * 12/1954 Shepherd ............ A61M 5/1417
                                                24/339
5,118,127 A *  6/1992 Partington ............... A61G 7/05
                                                280/483
(Continued)

FOREIGN PATENT DOCUMENTS

WO     WO-0193795 A2 * 12/2001 ........... A61G 12/008
WO  WO-2008042346 A2 *  4/2008 ........... A61G 12/004
(Continued)

OTHER PUBLICATIONS

International Search Report and Written Opinion issued to PCT/US20/60974, dated Feb. 9, 2021.
(Continued)

*Primary Examiner* — James A Shriver, II
*Assistant Examiner* — Ian Bryce Shelton
(74) *Attorney, Agent, or Firm* — Barnes & Thornburg LLP

(57) ABSTRACT

An accessory attachment mechanism for a wagon is provided. The mechanism has a mounting bracket, a pivot arm, and a retention mechanism. The mounting bracket is connected to the wagon and has a first opening, a second opening, and a pivot member. The pivot arm is pivotally connected to the mounting bracket at the pivot member and pivots about a plane generally parallel to a base of the wagon between a storage position and a use position. A pin extends through the pivot arm into separate openings in the mounting bracket to retain the pivot arm in the storage and use positions. The retention mechanism is provided at an end of the pivot arm and has a moveable clamp member adapted to secure an accessory thereto.

19 Claims, 9 Drawing Sheets

(58) Field of Classification Search
CPC ..... B62B 2207/00; B62B 3/007; B62B 3/102;
B62B 3/025; B62B 3/04; B62B 3/10;
B62B 1/12; B62B 3/02; B62B 5/087;
B62B 2207/02; B62B 5/0079; B62B
5/0016; B62B 5/002; A61G 2203/80;
A61G 2200/14; A61G 2203/78; B62K
27/12; B62K 27/003; B62K 13/02; B60D
1/143; B60D 1/173; B60D 1/145
See application file for complete search history.

(56) References Cited

U.S. PATENT DOCUMENTS

| | | | | |
|---|---|---|---|---|
| 5,219,139 | A * | 6/1993 | Hertzler | A61G 5/10 248/276.1 |
| 6,764,092 | B1 * | 7/2004 | Greaves, Jr. | B60D 3/00 280/402 |
| 7,258,310 | B2 * | 8/2007 | Norris | A61G 5/10 248/125.7 |
| 8,308,406 | B2 * | 11/2012 | Parks | A61G 5/10 410/7 |
| 8,870,209 | B2 * | 10/2014 | Conrad | B60D 1/167 280/33.996 |
| 10,052,254 | B2 * | 8/2018 | Chen | A61H 3/04 |
| 2003/0062705 | A1 * | 4/2003 | Britton | B62K 27/12 280/204 |
| 2007/0267556 | A1 * | 11/2007 | Herskovic | F16M 11/06 248/218.4 |
| 2011/0121149 | A1 * | 5/2011 | Herskovic | A61G 7/0503 248/223.41 |
| 2015/0090845 | A1 * | 4/2015 | Trelford | F16M 11/10 248/65 |
| 2016/0000995 | A1 | 1/2016 | Blankenship et al. | |
| 2016/0302982 | A1 * | 10/2016 | Blankenship | A61M 5/1415 |
| 2017/0215979 | A1 * | 8/2017 | Childs | H01R 13/639 |
| 2018/0186395 | A1 * | 7/2018 | Anderson | A61G 5/1037 |
| 2019/0195252 | A1 * | 6/2019 | Pryor | F16B 2/12 |
| 2019/0380894 | A1 * | 12/2019 | Ellis | B60D 1/52 |
| 2020/0390969 | A1 * | 12/2020 | Pearson | A61G 12/008 |

FOREIGN PATENT DOCUMENTS

| | | | | |
|---|---|---|---|---|
| WO | WO-2014156519 | A1 * | 10/2014 | ............... A61G 5/10 |
| WO | WO-2018226495 | A1 * | 12/2018 | ............. A61B 90/60 |
| WO | WO-2019180721 | A1 * | 9/2019 | ........... B62B 5/0016 |

OTHER PUBLICATIONS

"Brady Buggy Wagon," accessed online at: https://bit.ly/3udOQuL (available at least as early as Apr. 17, 2019).

"Wunderwagon—HC I.V. Trailer," accessed online at: https://bit.ly/2Nlq6KE (available at least as early as Apr. 17, 2019).

* cited by examiner

INTRAVENOUS DEVICE ATTACHMENT MECHANISM FOR WAGONS

CROSS-REFERENCE TO RELATED APPLICATIONS

This application claims the benefit of U.S. Provisional Patent Application No. 62/936,926 filed Nov. 18, 2019, which is expressly incorporated herein by reference and made a part hereof.

FEDERALLY SPONSORED RESEARCH OR DEVELOPMENT

Not Applicable.

TECHNICAL FIELD

The present subject matter relates to an accessory attachment mechanism for wagons, and more particularly, to an attachment mechanism for connecting an IV pole to a wagon.

BACKGROUND

Conventionally, children enjoy the entertainment and comfort of transportation in a wagon. This general sentiment extends to children in special circumstances and settings. These special settings and circumstances include hospitals and children needing to receive intravenous (IV) fluids/medications. Children in these settings are occasionally transported in wagons to improve their positive perception of the circumstances. Often times, it is not practical to interrupt treatment for children being transporting by wagon.

Typically, IV fluids/medications are administered from bags hanging on upright, vertical IV poles. Also, occasionally, pumps and/or other form factors are attached to vertical IV poles. IV poles often have a wide (relative to the vertical pole), stable base. Monitoring sensors, such as pulse and respiration monitors may similarly be hung from or mounted to IV poles. It may be difficult to move a child in a wagon along with an IV pole administering medicine/fluids to that child. More than one nurse or other hospital staff person may be needed to perform the dual tasks of pulling the wagon and transporting the IV pole and accompanying treatment materials. In another negative scenario, treatment may be interrupted unnecessarily during transport.

IV pole attachment mechanisms for wagons are known in the art. While such attachment mechanisms according to the prior art provide a number of advantages, they nevertheless have certain limitations. The present disclosure seeks to overcome certain of those limitations and other drawbacks of the prior art, and to provide new features not heretofore available. A full discussion of the features and advantages of the present disclosure is deferred to the following detailed description, which proceeds with reference to the accompanying drawings.

SUMMARY

According to certain aspects of the present disclosure, the disclosed subject technology relates to an accessory attachment mechanism for a wagon, including for securing an IV pole thereto.

The disclosed technology further relates to an accessory attachment mechanism for a wagon having a frame, comprising: a mounting bracket connected to the frame of the wagon, the mounting bracket having a first opening, a second opening, and a pivot member; a pivot arm having a first end and a second end, the first end of the pivot arm being pivotally connected to the mounting bracket at the pivot member, the pivot arm pivoting between a storage position and a use position; a pin connected to the pivot arm, the pin having a knob at a first end thereof, the pin extending into the first opening of the mounting bracket when the pivot arm is in the storage position, the pin extending into the second opening of the mounting bracket when the pivot arm is in the use position, and the pin being retractable from the first and second openings to allow the pivot arm to transition therebetween; an end cap connected to the pivot arm at the first end thereof, the end cap extending beyond the first end of the pivot arm, the end cap having a stop that engages the mounting bracket in the use position to prevent over-rotation of the pivot arm; and, a retention mechanism at the second end of the pivot arm, the retention mechanism having a moveable clamp member adapted to secure an accessory thereto.

The disclosed technology further relates to an accessory attachment mechanism for a wagon, comprising: a mounting bracket connected to the wagon, the mounting bracket having a first opening, a second opening, and a pivot member; a pivot arm having a first end and a second end, the first end of the pivot arm being pivotally connected to the mounting bracket at the pivot member, the pivot arm pivoting about a plane generally parallel to a base of the wagon between a storage position and a use position; a pin extending through the pivot arm, the pin extending into the first opening of the mounting bracket when the pivot arm is in the storage position, the pin extending into the second opening of the mounting bracket when the pivot arm is in the use position, and the pin being retractable from the first and second openings to allow the pivot arm to transition therebetween; and, a retention mechanism at the second end of the pivot arm, the retention mechanism having a moveable clamp member adapted to secure an accessory thereto.

The disclosed technology further relates to an accessory attachment mechanism for a wagon, comprising: a mounting bracket connected to the wagon, the mounting bracket having a first opening, a second opening, and a pivot member; a pivot arm having a first end and a second end, the first end of the pivot arm being pivotally connected to the mounting bracket at the pivot member, the pivot arm pivoting between a storage position and a use position, wherein the pivot arm pivots between 40° and 80° when pivoted from the storage position to the use position; a spring pin connected to the pivot arm, the pin extending into the first opening of the mounting bracket when the pivot arm is in the storage position, the pin extending into the second opening of the mounting bracket when the pivot arm is in the use position, and the pin being retractable from the first and second openings to allow the pivot arm to transition therebetween; and, a retention mechanism at the second end of the pivot arm, the retention mechanism having a moveable clamp member adapted to secure an accessory thereto.

The disclosed technology further relates to an accessory attachment mechanism wherein the pivot arm pivots about a plane generally parallel to a base of the wagon.

The disclosed technology further relates to an accessory attachment mechanism wherein the first end and the second end of the pivot arm are adjacent the wagon frame when the pivot arm is in the storage position.

The disclosed technology further relates to an accessory attachment mechanism wherein the pivot arm is pivoted away from the wagon in the use position.

The disclosed technology further relates to an accessory attachment mechanism wherein the pivot arm pivots between 40° and 80° when transitioned from the storage position to the use position.

The disclosed technology further relates to an accessory attachment mechanism wherein the pivot arm has an opening to receive the pin, the opening retaining a spring to bias the pin into the first opening of the mounting bracket and the second opening of the mounting bracket, respectively.

The disclosed technology further relates to an accessory attachment mechanism wherein the mounting bracket has a bottom plate, and wherein the first opening and second opening of the mounting bracket are provided in the bottom plate of the mounting bracket.

The disclosed technology further relates to an accessory attachment mechanism wherein the pin connected to the pivot arm extends through the end cap.

The disclosed technology further relates to an accessory attachment mechanism wherein the clamp member of the retention mechanism is connected to a threaded rod with a knob opposing the clamp member, and wherein turning of the knob in one direction moves the clamp member toward a stationary end of the retention mechanism to clamp an accessory therebetween.

The disclosed technology further relates to an accessory attachment mechanism further comprising an end cap connected to the pivot arm at the first end thereof, the end cap extending beyond the first end of the pivot arm, the end cap engaging the mounting bracket in the use position to prevent over-rotation of the pivot arm.

The disclosed technology further relates to an accessory attachment mechanism, wherein the mounting bracket is connected to a rear portion of a frame of the wagon.

The disclosed technology further relates to an accessory attachment mechanism, wherein the pivot arm has an opening to receive the pin, the opening retaining a spring to bias the pin into the first opening of the mounting bracket and the second opening of the mounting bracket, respectively, and wherein the pin has a knob at a first end thereof.

It is understood that other embodiments and configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

To understand the present disclosure, it will now be described by way of example, with reference to the accompanying drawings in which embodiments of the disclosures are illustrated and, together with the descriptions below are incorporated in and constitute a part of this specification, and serve to explain the principles of the disclosure. In the drawings.

Figure 1:
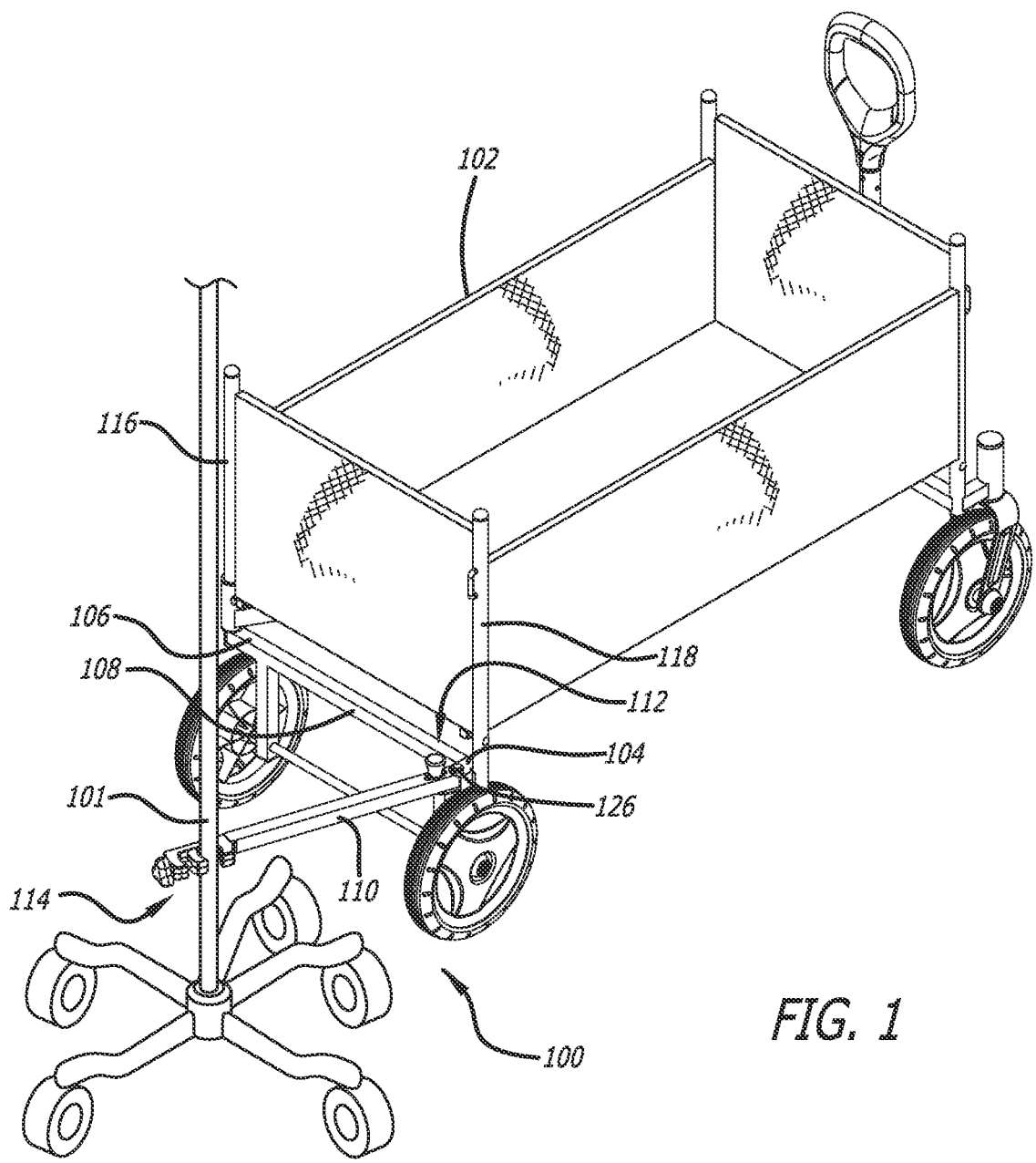
FIG. 1 is a rear top perspective view of a wagon having an accessory attachment mechanism according to the present disclosure.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

While this disclosure is susceptible of embodiments in many different forms, there is shown in the drawings and will herein be described in detail preferred embodiments with the understanding that the present disclosure is to be considered as an exemplification of the principles of the disclosure and is not intended to limit the broad aspect of the disclosure to the embodiments illustrated. It should be noted that the features illustrated in the drawings are not necessarily drawn to scale, and features of one embodiment may be employed with other embodiments as one of ordinary skill in the relevant art would recognize, even if not explicitly stated herein. Further, descriptions of well-known components and processing techniques may be omitted so as to not unnecessarily obscure the embodiments of the present disclosure. The examples used herein are intended merely to facilitate an understanding of ways in which the present disclosure may be practiced and to further enable those of ordinary skill in the art to practice the embodiments of the present disclosure. Accordingly, the examples and embodiments herein should not be construed as limiting the scope of the present disclosure, which is defined solely by the appended claims and applicable law.

Generally, this disclosure describes an accessory attachment mechanism for a wagon, such as for coupling an IV apparatus to a wagon. The accessory attachment mechanism may be operably coupled to a wagon frame for use in medical and/or therapeutic settings, such as in a hospital or treatment center. Preferably, the accessory attachment mechanism holds an IV pole such that the IV apparatus may be easily and conveniently transported along with a wagon carrying a patient associated with and, typically, attached by tubing and/or other medical devices to an IV bag hanging from the IV pole. In various embodiment, the wagon accessory attachment mechanism is configured to extend away from a wagon frame to accommodate different sizes and configurations of IV poles, such as IV poles having a base, a battery pack, and/or other bulky components. Likewise, a retention mechanism is configured to accept and hold IV poles of varying shape and size.

Referring now to the figures, and initially to FIGS. 1-4, there is shown an accessory attachment mechanism 100 for a wagon 102. In one embodiment, the accessory attachment mechanism 100 is used to couple an IV apparatus/pole 101 to the wagon 102. In one embodiment, the accessory attachment mechanism 100 comprises a mounting bracket 104 connected to the wagon 102, a pivot arm 110, a pivot mechanism 112, and a retention mechanism 114.

In one embodiment where the wagon 102 has a frame 106, the accessory attachment mechanism 100 is preferably mounted to the wagon frame 106, such as at the rear portion of the frame 106. For example, referring to FIG. 4, in one embodiment a cross member 108 of the wagon frame 106 is arranged between first and second vertical frame members 116, 118 of the wagon frame 106. And, the attachment mechanism 100 is mounted to the cross member 108 of the wagon frame 106, although this need not be the case in all contemplated embodiments, including where no wagon frame 106 is provided such as with a plastic or wood wagons.

Figure 2:
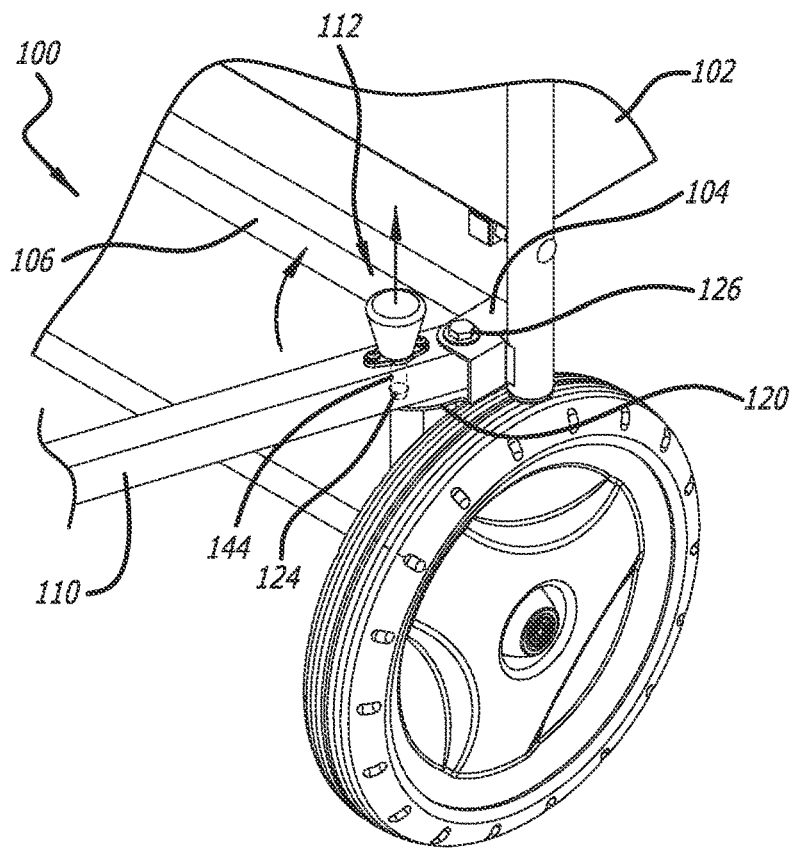
FIG. 2 is a partial perspective view of the accessory attachment mechanism of FIG. 1 with the pivot arm in the use position.
Figure 3:
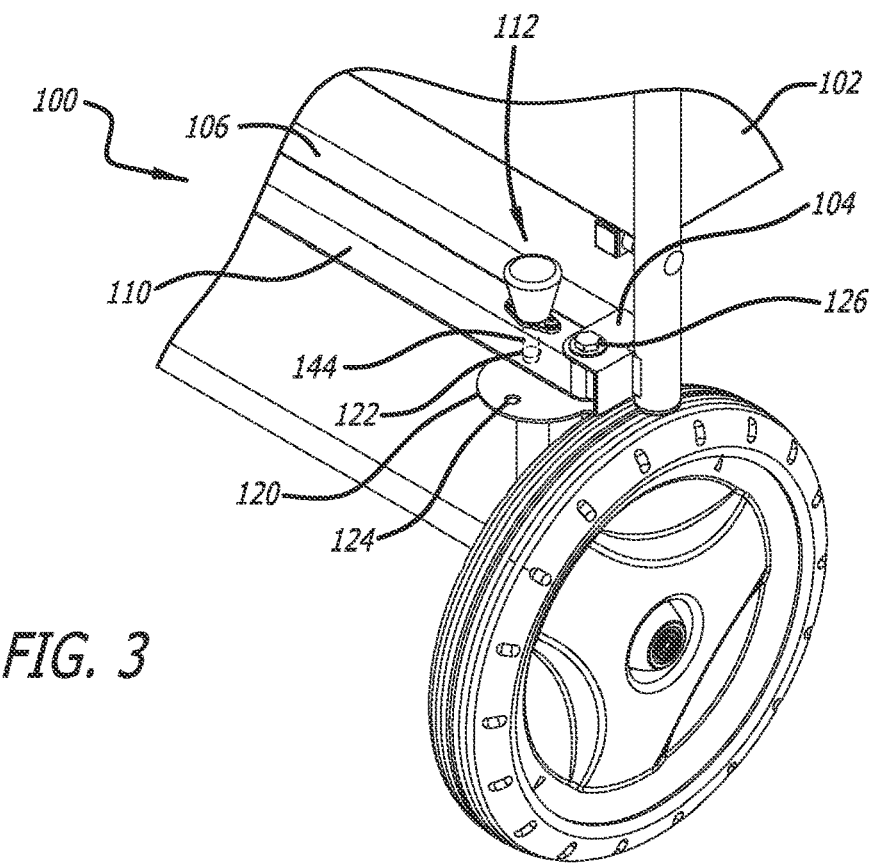
FIG. 3 is a partial top perspective view of the accessory attachment mechanism of FIG. 1 with the pivot arm in the storage position.
Figure 5:
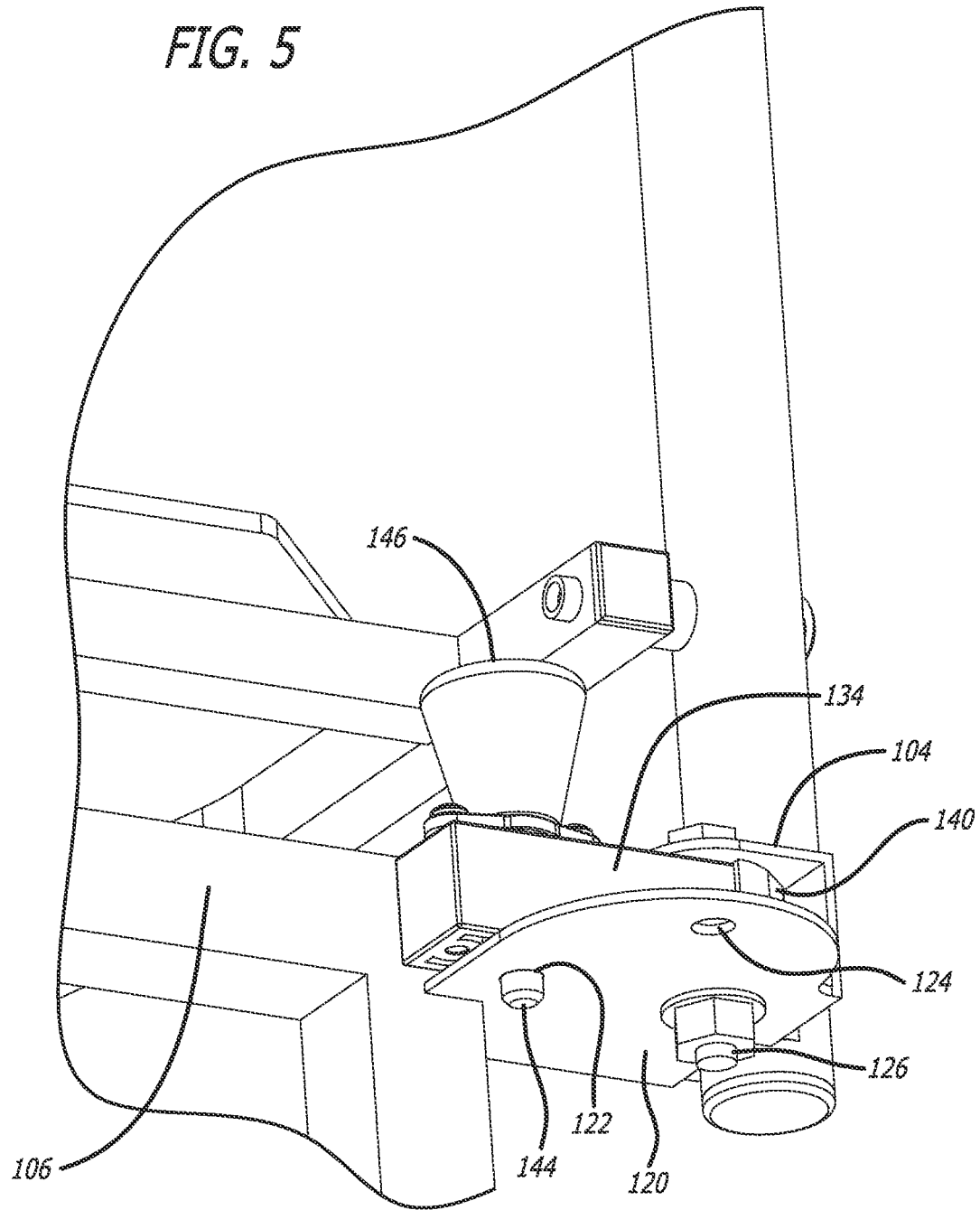
FIG. 5 is a partial bottom perspective view of the mounting bracket and pivot arm of the accessory attachment mechanism of FIG. 1.
Figure 6:
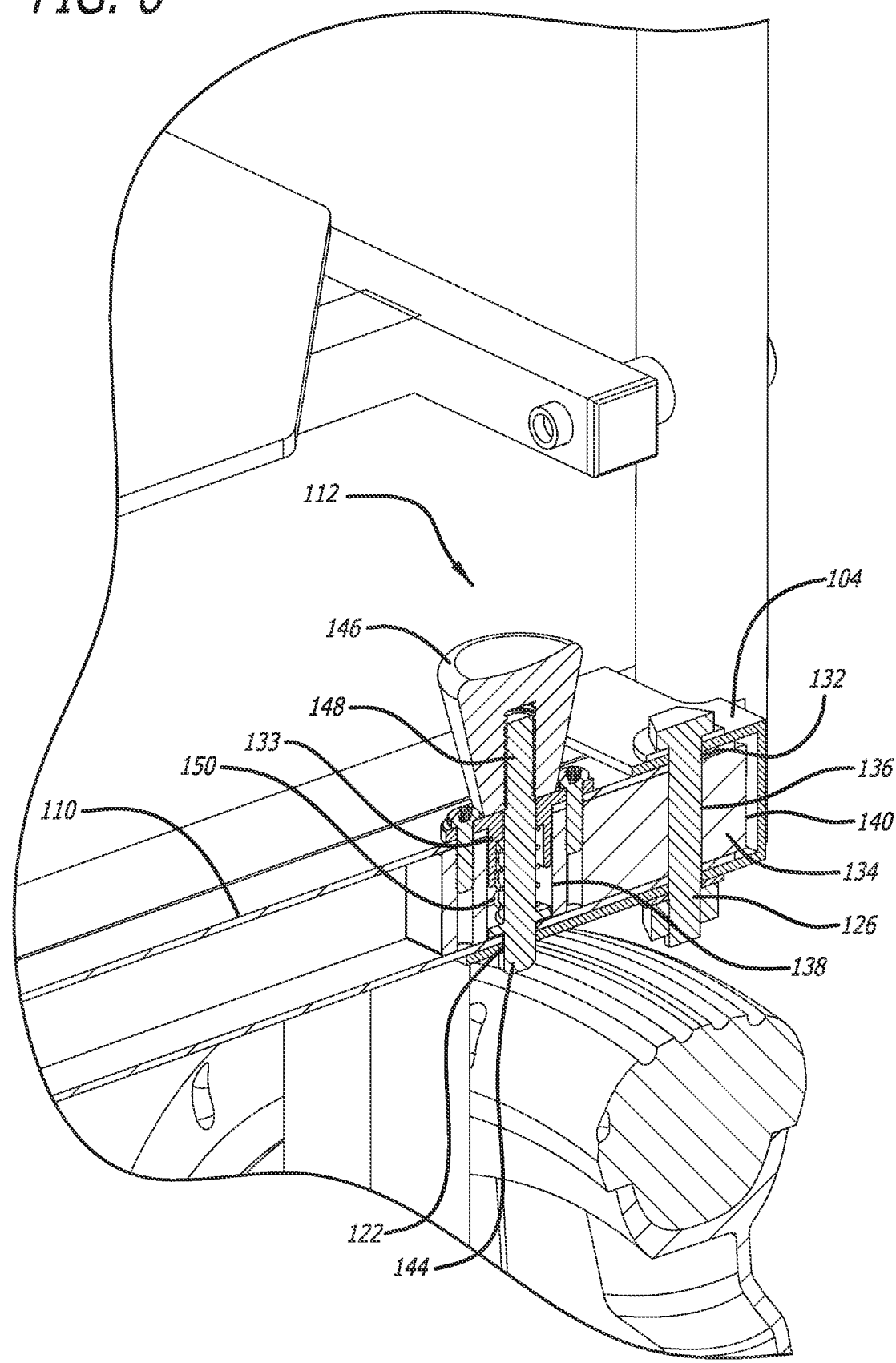
FIG. 6 is a partial perspective view in cross-section of the pivot arm and mounting bracket of the accessory attachment mechanism of FIG. 1.
Figure 7:
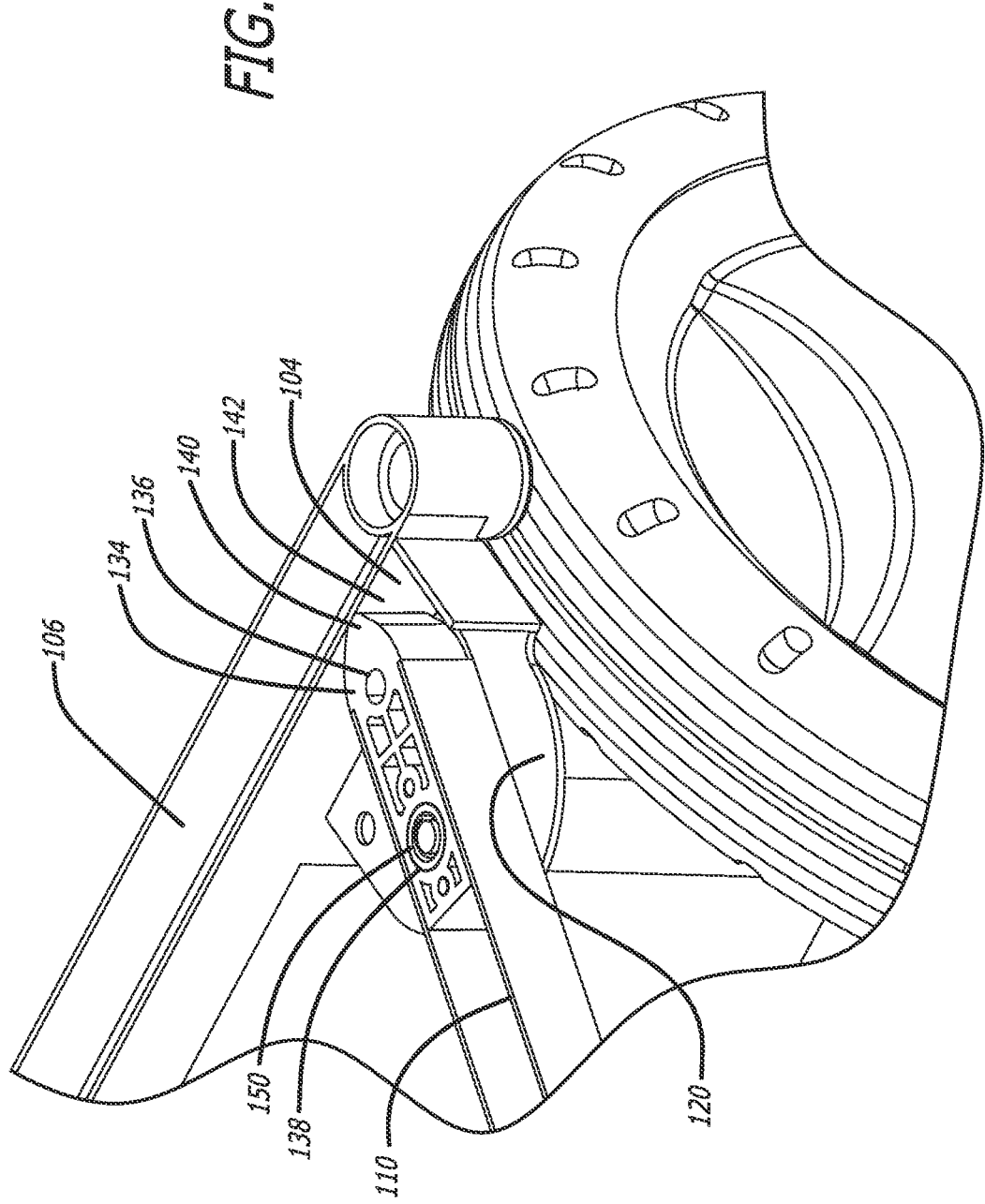
FIG. 7 is a partial perspective view of the pivot arm and mounting bracket of the accessory attachment mechanism of FIG. 1 in the use position, with top portions of the pivot arm and mounting bracket removed.
Figure 8:
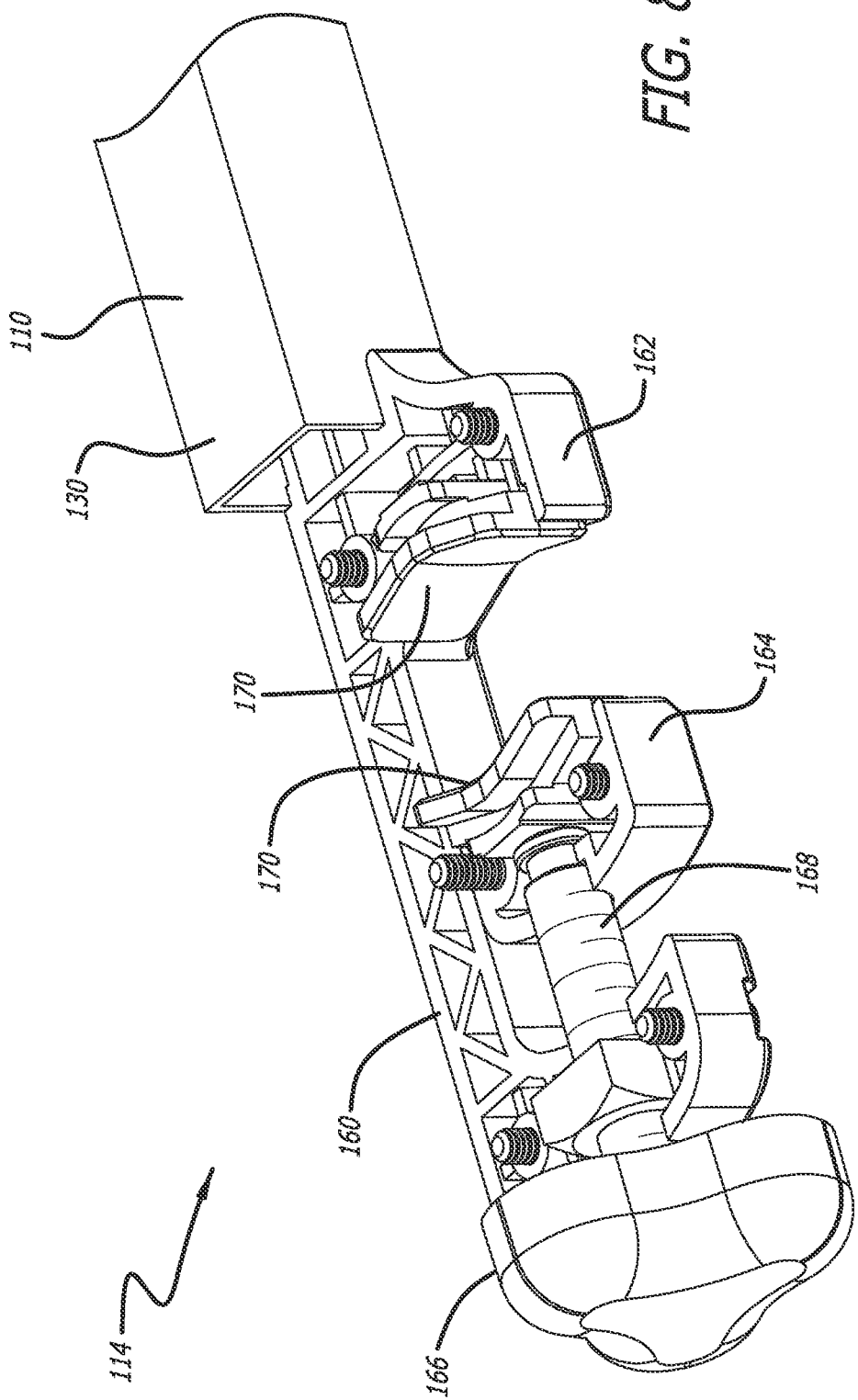
FIG. 8 is a perspective view of the retention mechanism of FIG. 1 with the top housing removed.
Figure 9:
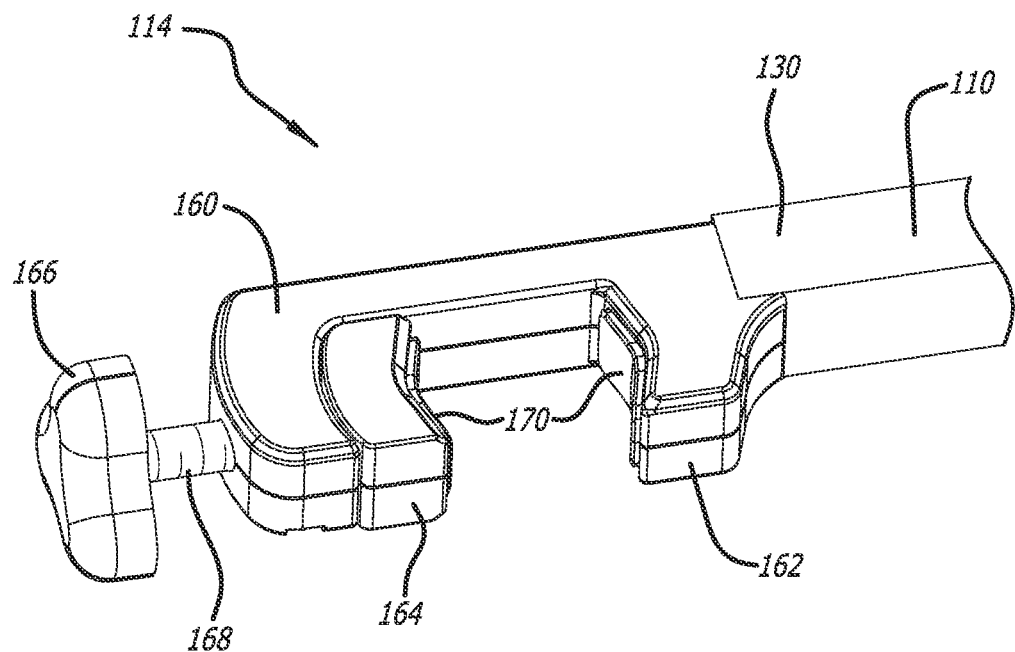
FIG. 9 is a perspective view of the retention mechanism of FIG. 1 in the open position.
Figure 10:
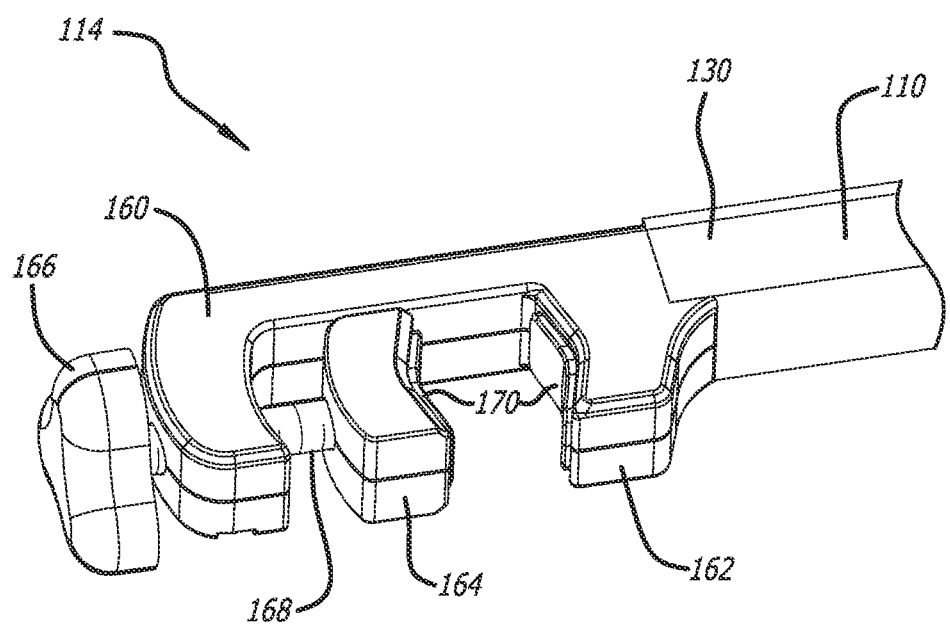
FIG. 10 is a perspective view of the retention mechanism of FIG. 1 in a clamped position.
Figure 11:
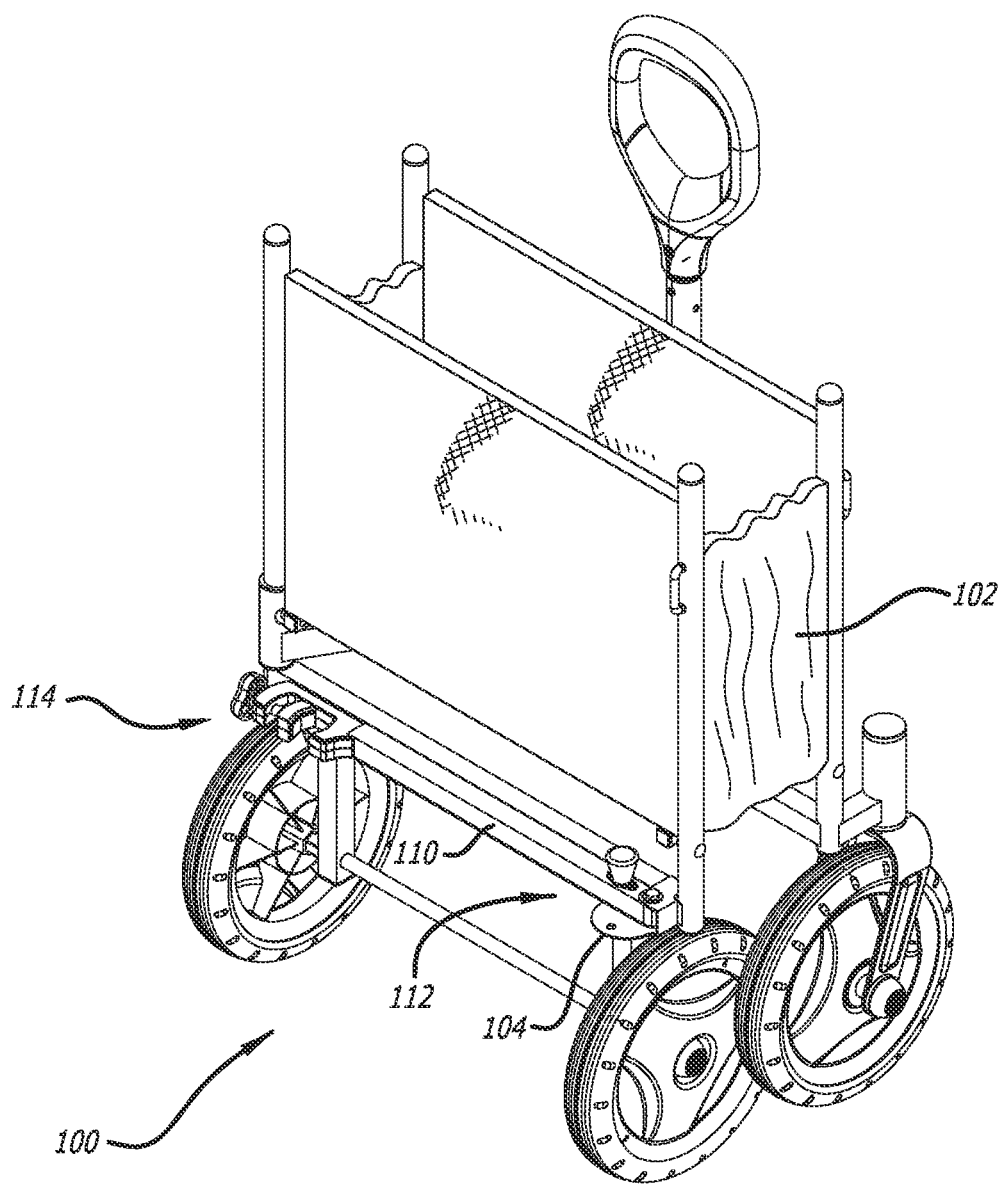
FIG. 11 is a rear perspective view of the accessory attachment mechanism in the storage position and the wagon in a folded configuration.

In a preferred embodiment, the pivot arm 110 of the accessory attachment mechanism 100 can be manipulated or pivoted between a use position, as shown in FIGS. 1, 2 and 7, and a storage position, as shown in FIGS. 3-6 and 11. In one embodiment, when the pivot arm 110 is in the storage position the pivot arm 110 is disposed adjacent the wagon body or wagon frame 106, including, in an illustrative embodiment, the cross member 108 of the wagon frame 106 as shown in the figures.

Preferably, the mounting bracket 104 is connected to one of the wagon or the wagon frame 106. The mounting bracket 104 may be fixed, such as via welding, fasteners, etc. to the wagon frame 106 or wagon body. In one embodiment, the mounting bracket 104 has a bottom plate 120 with a first opening 122 and a second opening 124 (see FIG. 5). Additionally, in a preferred embodiment the mounting bracket 104 has a pivot member 126 to pivotally connect the pivot member 110 to the pivot member 126 and thus the mounting bracket 104. As shown in FIGS. 5 and 6, the pivot member 126 may be a shaft, bolt, or some other component that allows the pivot member 110 to be pivotally connected thereto.

In one embodiment, the pivot arm 110 has a first end 128 and a second end 130. The pivot arm 110 is typically an elongated member, such as, for example, a tubular member, shaft, rod, bar, etc. As shown in the figures, the first end 128 of the pivot arm 110 is pivotally connected to the mounting bracket 104 at the pivot member 126. For example, the pivot arm 110 may have an opening 132 at the first end 128 thereof, through which the pivot member 126 passes to pivotally secure the pivot arm 110 to the mounting bracket 104 via the pivot member 126. Additionally, as explained herein, the pivot arm 110 will also typically have a second opening 133 through which a portion of the pivot mechanism 112 passes.

In one embodiment, as shown in FIGS. 5-7, an end cap 134 is provided for the pivot arm 110. The end cap 134 may be connected to the pivot arm 110 at the first end 128 thereof. In one embodiment, the end cap 134 extends both inside the first end 128 of the pivot arm 110 as well as beyond the first end 128 of the pivot arm 110, however, this is not required. If the end cap 134 is provided internal to the pivot arm 110, the end cap 134 will typically have a first opening 136 that mates with the opening 132 of the pivot arm 110 to allow the pivot member 126 to pass through both the pivot arm 110 and the end cap 134. Similarly, depending on the depth of the end cap 134 within the pivot arm 110, the end cap 134 may also have a second opening 138 that mates with the second opening 133 of the pivot arm 110 to allow the pivot mechanism 112 to pass through and partially reside therein. Further, in one embodiment the end cap 134 has a stop 140 that engages the mounting bracket 104 to prevent over-rotation of the pivot arm 110 when the pivot arm 110 is pivoted from the storage position to the use position as shown in FIG. 7. As shown in FIG. 7, when the pivot arm 110 is pivoted about the pivot member 126 to transition the pivot arm 110 from the storage position to the use position, the end or stop 140 of the end cap 134 will engage a surface 142 of the mounting bracket 104 to thereby stop or prevent additional pivoting motion of the pivot arm 110. This engagement of the stop 140 of the end cap 134 with the surface 142 of the mounting bracket 104 typically occurs when the pivot arm 110 is pivoted to the use position as shown in FIG. 7.

As explained herein, the accessory attachment mechanism 100 also has a pivot mechanism 112. In one embodiment, the pivot mechanism 112 includes a pin 144, such as a spring pin, that is connected to and extends through the pivot arm 110 and is adapted to engage the openings 122, 124 of the mounting bracket 104 to releasably retain the pivot arm 110 in the use position and the storage position. In alternate embodiments, the pivot mechanism 112 may include a knob 146 connected to a first end 148 of the pin 144 and a spring 150.

In one embodiment, the pin 144 of the pivot mechanism 112 is seated within the second opening 133 of the pivot arm 110 as shown in FIG. 6. Additionally, in a preferred embodiment, the pin 144 of the pivot mechanism 112 also passes through the second opening 138 of the end cap 134 that mates with the second opening 133 of the pivot arm 110. Further, as shown in FIG. 6, in a preferred embodiment, the spring 150 also resides in the second opening 133 of the pivot arm 110 and the second opening 138 of the end cap 134 to bias the pin 144 out the bottom of the pivot arm 110 and toward the bottom plate 120 of the mounting bracket 104.

As shown in FIGS. 1-6, when the pivot arm 110 is in the storage position the pin 144 will extend out of the pivot arm 110 and into the first opening 122 in the bottom plate 120 of the mounting bracket 104. To transition the pivot arm 110 from the storage position to the use position, the user lifts up on the pin 144, such as by lifting the knob 146, against the spring force of the spring 150, to lift the pin 144 out of the first opening 122 in the bottom plate 120 of the mounting bracket 104. The user can then pivot the pivot arm 110 away from the wagon 102 and toward the use position. When the pivot arm 110 is pivoted such that it is aligned with or in the use position, the spring 150 will bias the pin 144 into the second opening 124 in the bottom plate 120 of the mounting bracket 104 to retain the pivot arm 110 in the use position. Further, when the pivot arm 110 is aligned with the second opening 124 in the bottom plate 120 of the mounting bracket 104 the end or stop 140 of the end cap 134 will engage a surface 142 of the mounting bracket 104 to thereby stop or prevent additional pivoting motion of the pivot arm 110. Thus, the pin 144 is retractable from the first and second openings 122, 124 to allow the pivot arm 110 to transition therebetween.

Figure 4:
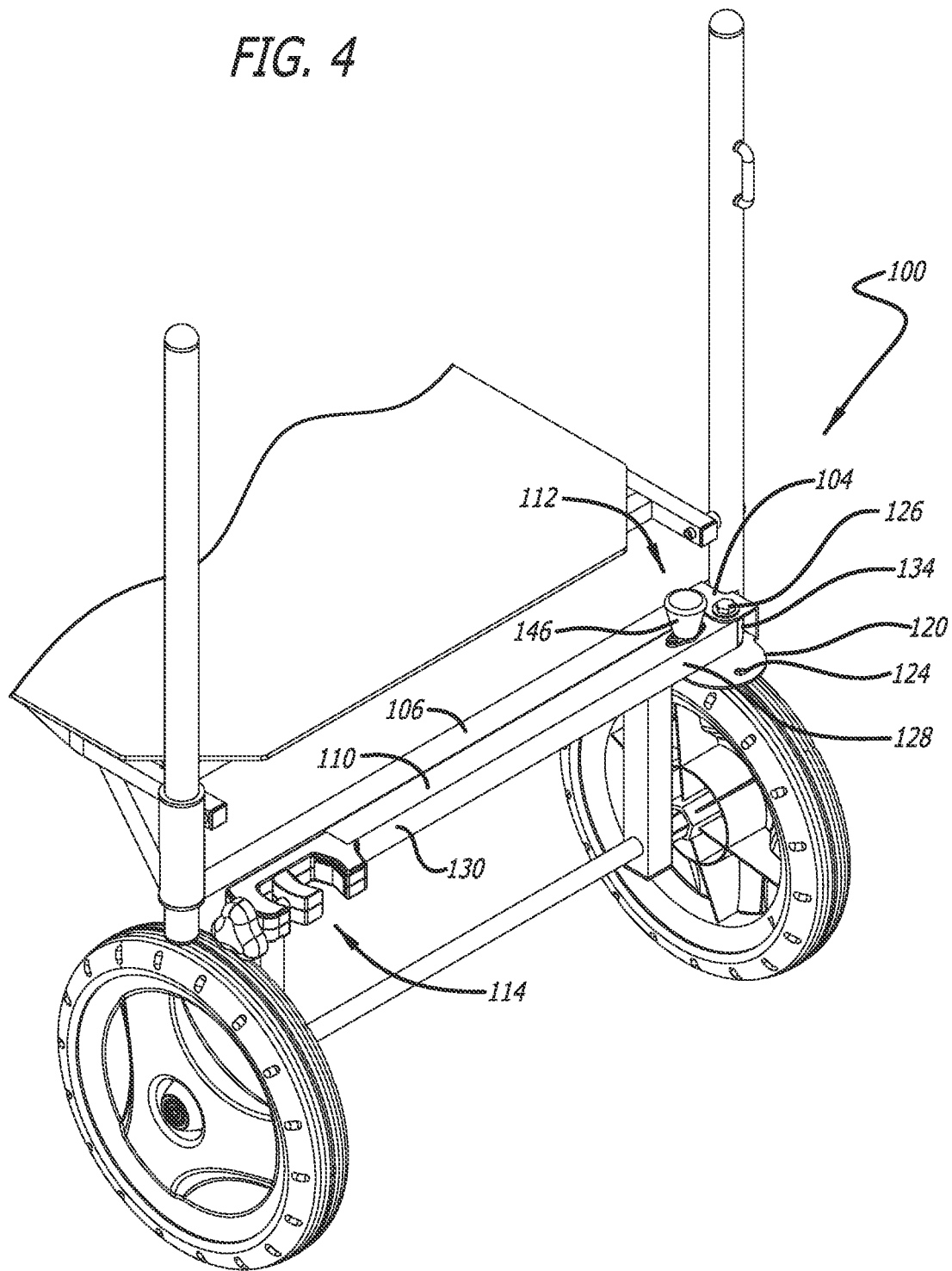
FIG. 4 is a partial top perspective view of the accessory attachment mechanism of FIG. 1 with the pivot arm in the storage position, and also showing a retention mechanism at a second end of the pivot arm.

As shown in the figures, including for example FIG. 4, in the storage position the first end 128 and the second end 130 of the pivot arm 110 are adjacent the wagon frame 106 when the pivot arm 110 is in the storage position. To move the pivot arm 110 to the use position the pivot arm 110 is pivoted about a horizontal plane that is generally parallel to the base on the wagon as well as to the floor on which the wagon resides. In a preferred embodiment, the pivot arm generally pivots between 40° and 80° to transition from the storage position to the use position.

Referring now to FIGS. 1 and 8-10, an exemplary embodiment of the retention mechanism 114 is illustrated. The retention mechanism 114 is preferably connected to the second end 130 of the pivot arm 110. In one embodiment, the retention mechanism 114 comprises a housing 160 with a fixed or stationary clamp member 162 and a moveable clamp member 164. The moveable clamp member 164 may be adjusted with a screw-type mechanism operable by a user of the wagon accessory attachment mechanism 100. A knob 166 connected to a threaded member 168 is turned to linearly move the moveable clamp member 164, thereby increasing or decreasing the space between the fixed clamp member 162 and the moveable clamp member 164 and correspondingly tightening or loosening the grip on the component, such as an IV apparatus/pole 101 situated between the clamp members 162, 164. Accordingly, the moveable clamp ember 164 may tighten about different sizes of IV poles and/or tubes to securely hold IV apparatuses of varying size and shape. In a preferred embodiment, the clamp members 162, 164 have rubber inserts 170 at their ends to provide a more secure tightening against the IV pole 101 therebetween.

The embodiment(s) detailed hereinabove may be combined in full or in part, with any alternative embodiment(s) described.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Numerous modifications to the present disclosure will be apparent to those skilled in the art in view of the foregoing description. Preferred embodiments of this disclosure are described herein, including the best mode known to the inventors for carrying out the disclosure. It should be understood that the illustrated embodiments are exemplary only, and should not be taken as limiting the scope of the disclosure.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. Additionally, the terms "first," "second," "third," and "fourth" as used herein are intended for illustrative purposes only and do not limit the embodiments in any way. Further, the term "plurality" as used herein indicates any number greater than one, either disjunctively or conjunctively, as necessary, up to an infinite number. Additionally, the term "having" as used herein in both the disclosure and claims, is utilized in an open-ended manner.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying Claims.

Further, the claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

INDUSTRIAL APPLICABILITY

The accessory attachment mechanism may hold medical devices or other components other than IV poles. Further, the accessory attachment mechanism may, in certain embodiments, hold IV poles that do not accompany IV apparatuses, but, instead, are connected to other components such as medical equipment.

What is claimed is:

1. An accessory attachment mechanism for a wagon having a frame, comprising:
    a mounting bracket connected to the frame of the wagon, the mounting bracket having a first opening, a second opening, and a pivot member;
    a pivot arm having a first end and a second end, the first end of the pivot arm being pivotally connected to the mounting bracket at the pivot member, the pivot arm pivoting between a storage position and a use position;
    a pin connected to the pivot arm, the pin having a knob at a first end thereof, the pin extending into the first opening of the mounting bracket when the pivot arm is in the storage position, the pin extending into the second opening of the mounting bracket when the pivot arm is in the use position, and the pin being retractable from the first and second openings to allow the pivot arm to transition therebetween;
    an end cap connected to the pivot arm at the first end thereof, the end cap extending beyond the first end of the pivot arm, the end cap having a stop that engages the mounting bracket in the use position to prevent over-rotation of the pivot arm; and,
    a retention mechanism at the second end of the pivot arm, the retention mechanism having a moveable clamp member adapted to secure an accessory thereto.

2. The accessory attachment mechanism of claim 1, wherein the pivot arm pivots about a plane generally parallel to a base of the wagon.

3. The accessory attachment mechanism of claim 1, wherein the first end and the second end of the pivot arm are adjacent the wagon frame when the pivot arm is in the storage position.

4. The accessory attachment mechanism of claim 1, wherein the pivot arm is pivoted away from the wagon in the use position.

5. The accessory attachment mechanism of claim 4, wherein the pivot arm pivots between 40° and 80° when transitioned from the storage position to the use position.

6. The accessory attachment mechanism of claim 1, wherein the pivot arm has an opening to receive the pin, the opening retaining a spring to bias the pin into the first opening of the mounting bracket and the second opening of the mounting bracket, respectively.

7. The accessory attachment mechanism of claim 1, wherein the mounting bracket has a bottom plate, and wherein the first opening and second opening of the mounting bracket are provided in the bottom plate of the mounting bracket.

8. The accessory attachment mechanism of claim 1, wherein the pin connected to the pivot arm extends through the end cap.

9. The accessory attachment mechanism of claim 1, wherein the clamp member of the retention mechanism is connected to a threaded rod with a knob opposing the clamp member, and wherein turning of the knob in one direction moves the clamp member toward a stationary end of the retention mechanism to clamp an accessory therebetween.

10. An accessory attachment mechanism for a wagon, comprising:
    a mounting bracket connected to the wagon, the mounting bracket having a first opening, a second opening, and a pivot member;
    a pivot arm having a first end and a second end, the first end of the pivot arm being pivotally connected to the mounting bracket at the pivot member, the pivot arm pivoting about a pivot arm plane generally parallel to a base of the wagon between a storage position and a use position;

a pin extending through the pivot arm entirely about a plane generally parallel to the pivot arm plane and into the first opening of the mounting bracket when the pivot arm is in the storage position, the pin extending into the second opening of the mounting bracket when the pivot arm is in the use position, and the pin being retractable from the first and second openings to allow the pivot arm to transition therebetween, the pin having a flange extending therefrom to operate as a stop against an interior surface of the pivot arm; and, a retention mechanism at the second end of the pivot arm, the retention mechanism having a moveable clamp member adapted to secure an accessory thereto.

11. The accessory attachment mechanism of claim 10, further comprising an end cap connected to the pivot arm at the first end thereof, the end cap extending beyond the first end of the pivot arm, the end cap engaging the mounting bracket in the use position to prevent over- rotation of the pivot arm.

12. The accessory attachment mechanism of claim 10, wherein the mounting bracket is connected to a rear portion of a frame of the wagon.

13. The accessory attachment mechanism of claim 10, wherein the pivot arm has an opening to receive the pin, the opening retaining a spring to bias the pin into the first opening of the mounting bracket and the second opening of the mounting bracket, respectively, and wherein the pin has a knob at a first end thereof.

14. The accessory attachment mechanism of claim 10, wherein the clamp member of the retention mechanism is connected to a threaded rod with a knob opposing the clamp member, and wherein turning of the knob in one direction moves the clamp member toward a stationary end of the retention mechanism to clamp an accessory therebetween.

15. An accessory attachment mechanism for a wagon, comprising:

a mounting bracket connected to the wagon, the mounting bracket having a first opening, a second opening, and a pivot member;

a pivot arm having a first end and a second end, the first end of the pivot arm being pivotally connected to the mounting bracket at the pivot member, the pivot arm pivoting between a storage position and a use position, wherein the pivot arm pivots between 40° and 80° when pivoted from the storage position to the use position;

a pin connected to the pivot arm, the pin extending into the first opening of the mounting bracket when the pivot arm is in the storage position, the pin extending into the second opening of the mounting bracket when the pivot arm is in the use position, and the pin being retractable from the first and second openings to allow the pivot arm to transition therebetween;

an end cap connected to the pivot arm at the first end thereof, the end cap extending beyond the first end of the pivot arm, the end cap having a stop that engages the mounting bracket in the use position to prevent over-rotation of the pivot arm; and, a retention mechanism at the second end of the pivot arm, the retention mechanism having a moveable clamp member adapted to secure an accessory thereto.

16. The accessory attachment mechanism of claim 15, wherein the pivot arm pivots about a plane generally parallel to a base of the wagon.

17. The accessory attachment mechanism of claim 15, wherein the mounting bracket is connected to a rear portion of a frame of the wagon.

18. The accessory attachment mechanism of claim 15, wherein the pivot arm has an opening to receive the pin, the opening retaining a spring to bias the pin into the first opening of the mounting bracket and the second opening of the mounting bracket, respectively, and wherein the pin has a knob at a first end thereof.

19. The accessory attachment mechanism of claim 15, wherein the clamp member of the retention mechanism is connected to a threaded rod with a knob opposing the clamp member, and wherein turning of the knob in one direction moves the clamp member toward a stationary end of the retention mechanism to clamp an accessory therebetween.

* * * * *